United States Patent [19]

Nemtsov et al.

[11] 4,035,271

[45] July 12, 1977

[54] METHOD OF REMOVING ACIDS FROM REACTION LIQUID OF DIMETHYL DIOXANE SYNTHESIS

[76] Inventors: Mark Semenovich Nemtsov, prospekt Gagarina, 21, kv. 8; Klavdia Mikhailovna Trenke, prospekt Rimskogo-Korsakova, 65, kv. 105; Moisei Isaakovich Ryskin, bulvar Krasnykh Zor 20, kv. 38; Maria Mikhailovna Kiseleva, ulitsa Telmana 32, korpus 3, kv. 5, all of Leningrad, U.S.S.R.

[21] Appl. No.: 245,612

[22] Filed: Apr. 19, 1972

[51] Int. Cl.² .................................. B01D 13/02
[52] U.S. Cl. ........................... 204/180 P; 204/301
[58] Field of Search ................... 204/180 P, 301

[56] References Cited

U.S. PATENT DOCUMENTS

| | | | |
|---|---|---|---|
| 3,063,924 | 11/1962 | Gomella | 204/180 P |
| 3,383,245 | 5/1968 | Scallet et al. | 204/180 P X |
| 3,507,764 | 4/1970 | Asahi et al. | 204/180 P |
| 3,663,417 | 5/1972 | Heit et al. | 204/301 |
| 3,673,068 | 6/1972 | Seko et al. | 204/180 P |

*Primary Examiner*—Arthur C. Prescott

[57] ABSTRACT

A method of removing acids from the aqueous reaction liquid wherein dimethyl dioxane is produced from isobutene and formaldehyde, characterized in that the aqueous reaction liquid is subjected to a two-step dialysis with a subsequent complete purification of the formed diluate by passing it through ion-exchange filters.

1 Claim, No Drawings

METHOD OF REMOVING ACIDS FROM REACTION LIQUID OF DIMETHYL DIOXANE SYNTHESIS

The present invention relates to the removal of acids present during the production of isoprene from isobutene and formaldehyde and, more particularly, to a method of removing acids from the reaction liquid of the synthesis of dimethyl dioxane-1,3, from which isoprene is formed.

It is known that, for the condensation reaction of isobutene with formaldehyde for producing dimethyl dioxane, which is an intermediate useful for isoprene production, strong mineral acids, preferably sulphuric acid, are used as a catalyst for this reaction. The latter, being present in the aqueous reaction liquid, called hereafter an "aqueous liquid", essentially complicates its re-processing wherein considerable technological difficulties are involved.

Thus, dimethyl dioxane (DMD) and other comparatively low boiling reaction products, present in the aqueous reaction liquid, as well as the unreacted formaldehyde, which is volatile only in excess of water vapor, should be distilled off at elevated temperatures, which in the presence of sulphuric acid and other strong acids results in a considerable development of undesirable secondary reactions, in particular, in the formation of resinous substances clogging the apparatus.

Therefore, the acidic liquid is subjected to a preliminary neutralization by alkali (NaOH) which results in the enrichment of the aqueous liquid with salts of the acid-catalyst ($Na_2SO_4$) and sodium formate (formic acid is formed in a small quantity as a by-product of isoprene synthesis, mainly at the stage of formaldehyde regeneration).

It was recently shown by us that it is reasonable to carry out the DMD synthesis at comparatively low temperatures, but with a consequent increase in the acid-catalyst concentration. In this case the neutralization of the latter in addition to a considerable increase in alkali consumption results in a still higher increase of the mineral salt content in the neutralized aqueous liquid.

Insofar as a fairly complete distilling-off of formaldehyde from the aqueous liquid requires a simultaneous distilling-off of a great amount of water, and even in case of small concentrations of acid-catalyst, there arises a danger of mineral salts precipitating in the rectification column.

But the use of the above-mentioned low-temperature process with a high acid content in the reaction aqueous liquid is practically impossible because of the total clogging of the column with salts.

Also no less difficulty arises during the withdrawal of high-boiling by-products (HBBP) of the DMD synthesis from the neutralized liquid.

Thus in the case of withdrawal of HBBP by extracting them by highly hydrophilic extraction agents effective for this particular case, the extraction solution containing highly hydrophilic components of HBBP: diols and triols turns out to be enriched with a great amount of water and, accordingly, with dissolved mineral salts. As a result, the distilling off of the extraction agent from the extraction solution in the rectification column is, in fact, also impracticable because of the precipitation of solid salts.

As a preventive measure against this phenomenon there may be used the distilling off of the extraction agent, in a step system of evaporators with a consequent removal of salts from every step (USSR Inventor's Certificate No. 210,851).

However, such a realization of the process is associated with considerable difficulties concerning the technological process and apparatus, the overcoming of which complicates the process and makes it more expensive.

The amount of salts which precipitate during the distilling off of the extraction agent can be considerably decreased, provided that HBBP extraction is carried out by a method of extracting with less hydrophilic solvents (USSR Inventor's Certificate No. 193,367). However, even in this case, apart from a great consumption of the extraction agent, the formed extraction solutions still contain up to 0.1% of mineral salts and higher, which excludes the use of conventional rectification columns for distilling off the extracting agent and, consequently, also predetermines the necessity of using a step system of evaporation mentioned above.

The removal of the acid itself or its salts from the aqueous liquid by means of the known method of ionite purification in this particular case is not practical because of a high content of the said substances in it and also because of a great amount of effluents coming out of ion exchangers in the ionite regeneration process.

Thus, none of the known embodiments of aqueous liquid processing enumerated above can be considered adequate for industrial application.

An object of the present invention is to provide a method of acid removal from the aqueous reaction liquid of DMD synthesis, free from the above-said disadvantages and, in particular, without recourse to acid neutralization by alkali.

Said object is accomplished by virtue of the present invention, the essence thereof being as follows.

The removal of both mineral (sulphuric) and formic acids is proposed to be performed by means of a combined process consisting of electrodialysis and an additional ion exchange purification, thereby completely obviating the necessity of acid neutralizing by alkali.

For electrodialysis use is made of conventional apparatus utilized for desalting mineralized water, but they are provided with cationite and anionite membranes made on an acid-resistant basis.

Electrodialyzers are a system consisting of diluate and concentration chambers separated from each other by cationite and anionite membranes.

For ensuring complete removal of mineral acid-catalyst from an acid aqueous liquid with its (mineral acid-catalyst) subsequent utilization there is used a system consisting of two steps of electrodialysis with a subsequent removal of the residual quantity of mineral acid from diluate by the known methods, for example, by means of ionite purification.

While the mineral acid that is removed can be returned to the synthesis, the formic acid that is also removed cannot be returned to the whole system, since its accumulation in the reaction cycle in not permissible. Therefore it is necessary to use a two-step electrodialysis system.

This last-mentioned task is solved owing to the fact that mobility of formic acid anion is considerably inferior to that of sulphuric acid anion, therefore in case of appropriate selection of the withdrawal depth of the latter, it is possible to adjust the formic acid concentration in the diluate and concentrate.

In the work carried out by the authors of this invention it has been shown that while, in the first step, 60–80% of the initial content of $H_2SO_4$ in the aqueous liquid is withdrawn, the corresponding amount of formic acid withdrawn is 20–40%. In the case of further electrodialysis at the second step of the system the amount of sulphuric acid removed is additionally from 30–35% to 10–15%, accompanied by the removal of formic acid from 50 to 30%, accordingly, from the diluate.

As a result, the total removal of sulfuric acid in both steps is 90–95%, while for formic acid it is about 70% of its original content in the aqueous liquid.

Thus, at the first step of the electrodialysis, most of the sulphuric acid-catalyst can be removed from the diluate with a comparatively small quantity of formic acid transferred to the concentrate solution, which makes it possible to return the removed mineral acid to the synthesis.

The mixture of mineral and formic acids removed during the second step can be let out from the system.

Thus the accumulation of formic acid in the reaction system is excluded, and its concentration in the aqueous liquid is not higher than 0.1–0.2%.

Subsequent complete removal of mineral (sulphuric) acid from the diluate of the second step, containing $H_2SO_4$ in an amount of 0.1–0.2% or less, is carried out either in conventional ionite filters or by using special methods of electrodialysis, for example, filling chambers with ionite granules.

In accordance with the above-said discussion, the process of acid removal from the aqueous liquid of DMD synthesis without neutralization is carried out in the following way.

In the first step of the electrodialysis, one or several successively installed electrodialyzers are employed, each having a diluate chamber and a concentration chamber. An acid aqueous liquid directly from the DMD synthesis reaction system is introduced into the diluate chamber(s); the concentration chambers are supplied with a liquid into which the acid removed from the diluate is transferred.

The most preferred embodiment of the first step of the process comprises use of the starting formaldehyde solution employed in the DMD synthesis as a concentration liquid. In this case the main quantity of the withdrawn sulphuric acid (60–80%) is directly returned to the DMD synthesis.

However, in individual cases it is possible to supply the concentration chambers of the first step dialyzer with water instead of the original formaldehyde solution, the aqueous solution of sulphuric acid being removed from the system for other applications.

In the second step of the electrodialysis, wherein one or more dialyzers are used, diluate from the first step comes to diluate chambers of the second step, and the concentration chambers are fed with pure water into which almost all sulphuric acid and a considerable part of formic acid are transferred. The concentrate solution coming out of the second step is either discharged into a sewer system or used for supplying the first step concentration chambers.

The total degree of mineral acid removal while using a two-step electrodialysis comes to 90–95%, while for the formic acid it comes to 70%. Residual acid concentrations in the final dialysate are: $H_2SO_4$ — 0.1–0.2% and lower, and HCOOH — 0.05 –0.08%.

The removal of the residual amount of acids, as mentioned above, is carried out means of conventional ionite filters or in electrodialyzers, filled with ionites. The sulphuric acid is removed practically completely and a small amount of the formic acid may be partly left in the diluate as it does not interfere with further diluate processing in order to remove DMD, HBBR and other valuable products from it.

For a better understanding of the essence of the present invention, an example is set hereinbelow.

The present invention may also be carried out under different conditions which are within the scope of the present method.

EXAMPLE

In diluate chambers of the first step dialyzer in which cationite membranes are made on the basis of Amberlite-1R120, a cationic resin containing sulfonic acid groups, and anionite membranes on the basis of Amberlite-1RA400, an anionic resin contain quaternary ammonium groups (said Amberlite resins being copolymers of styrene and divinybenzene and containing the respectively named functional groups) there is fed acid aqueous reaction liquid of the DMD synthesis, containing 3.3% $CH_2O$; 1.99% $H_2SO_4$ and 0.18% HCOOH.

In the dialyzer concentration chambers there is introduced the starting formaline solution containing 25.7% $CH_2O$ and 0.2% HCOOH. At temperatures of 20.0° C at the dialyzer inlet and 21.5° C at the dialyzer outlet, and at a current density of 10 $mA/cm^2$, there is discharged from the concentration chambers, a solution containing 23.6% $CH_2O$; 0.97% $H_2SO_4$ and 0.09% HCOOH. The exiting diluate contains: 2.9% $CH_2O$; 0.46% $H_2SO_4$ and 0.11% HCOOH.

The degree of $H_2SO_4$ removal from the aqueous liquid is 77% and that of HCOOH is 39%.

Current efficiency at the first step is 62% of the theoretical power consumption for the removed acids.

In the course of carrying out the second step of acid extraction the diluate from the first step is introduced into the diluate chambers of the electrodialyzer, and the desalted or desalinated water is fed into the concentration chambers. The temperature at the dialyzer inlet and outlet is 20±1° C at the current density of 4 $mA/cm^2$.

From the concentration chamber there is discharged the solution containing 0.4 $CH_2O$; 0.30% $H_2SO_4$ and 0.05% HCOOH. The discharged solution contains: 2.0% $CH_2O$; 0.16% $H_2SO_4$ and 0.06% HCOOH. The degree of $H_2SO_4$ removal is 72% and that of HCOOH, 50%.

Current efficiency of the second step of the electrodialysis is 33% of the theoretical power consumption.

The total acid removal in the two steps is 93% for $H_2SO_4$ and 70% for HCOOC.

The diluate from the second step is passed through anionite AB-17, the discharged aqueous liquid containing practically no sulphuric acid (qualitative test for $BaSO_4$ precipitation).

The reproducibility of results was checked for 40 cycles without scarcely any change in the anionite capacity.

What is claimed is:

1. A method of removing a mineral acid and an organic acid from an aqueous reaction liquid in which dimethyl-dioxane has been synthesized from isobutene and formaldehyde, comprising subjecting said aqueous reaction liquid to a two-step electrodialysis in which from about 60 to 80% of the mineral acid originally present and from about 20 to 40% of the organic acid originally present are removed after the first dialysis step, and from about 90 to 95% of the mineral acid originally present and from about 70 to 80% of the organic acid originally present are removed after the completion of both steps, the concentration liquid of the first step of electrodialysis being the original formaldehyde solution; and the concentration liquid of the second step being water.

* * * * *